United States Patent [19]
Hayashi et al.

[11] Patent Number: 6,053,058
[45] Date of Patent: *Apr. 25, 2000

[54] ATMOSPHERE CONCENTRATION MONITORING FOR SUBSTRATE PROCESSING APPARATUS AND LIFE DETERMINATION FOR ATMOSPHERE PROCESSING UNIT OF SUBSTRATE PROCESSING APPARATUS

[75] Inventors: Toyohide Hayashi; Hiroaki Sugimoto; Masaya Asai; Noriaki Yokono, all of Kyoto, Japan

[73] Assignee: Dainippon Screen Mfg. Co., Ltd., Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/938,900

[22] Filed: Sep. 26, 1997

[30] Foreign Application Priority Data

Sep. 30, 1996 [JP] Japan .................................... 8-280171
Sep. 30, 1996 [JP] Japan .................................... 8-280172

[51] Int. Cl.⁷ ........................................................ G01N 1/00
[52] U.S. Cl. ......................................................... 73/863.01
[58] Field of Search ......................... 73/31.01, 31.03, 73/863.01, 863.21, 863.23, 863.33, 863.83, 864.34, 864.81, 865.5; 340/627, 628, 632

[56] References Cited

U.S. PATENT DOCUMENTS

| | | |
|---|---|---|
| 3,678,487 | 7/1972 | Ludewig, Jr. et al. . |
| 4,764,758 | 8/1988 | Skala . |
| 5,281,816 | 1/1994 | Jacobson et al. . |
| 5,553,496 | 9/1996 | Nishiyama et al. .................... 73/865.5 |
| 5,756,262 | 5/1998 | Endo et al. . |

FOREIGN PATENT DOCUMENTS

| | | |
|---|---|---|
| 7-236814 | 9/1995 | Japan . |
| 8-222492 | 8/1996 | Japan . |

*Primary Examiner*—Robert Raevis
*Attorney, Agent, or Firm*—Ostrolenk, Faber, Gerb & Soffen, LLP

[57] ABSTRACT

An atmosphere concentration monitoring system includes multiple measurement ports for collecting atmospheric gas, a port selector for switching the multiple measurement ports, a concentration measurement unit for sampling the atmospheric gas through the selected measurement port and measuring the concentration of a specific substance contained in the sampled atmospheric gas. A different set of measurement conditions are established for each of the measurement ports. The port selector and the concentration measurement unit are controlled according to the different sets of measurement conditions. A life determination device includes a flow rate determination unit for measuring a flow rate of the atmospheric gas passing through the atmosphere processing unit. A throughput of the atmosphere processing unit is determined by integrating, with respect to time, a product of the flow rate and a difference between the upstream and downstream concentrations. The life of the atmosphere processing unit is determined as a function of the throughput.

7 Claims, 10 Drawing Sheets

ATMOSPHERE CONCENTRATION MONITORING FOR SUBSTRATE PROCESSING APPARATUS AND LIFE DETERMINATION FOR ATMOSPHERE PROCESSING UNIT OF SUBSTRATE PROCESSING APPARATUS

BACKGROUND OF THE INVENTION

1. Field of the Invention

This invention relates to atmosphere concentration monitoring for monitoring the concentrations of one or more specific substances in the atmosphere of a substrate processing apparatus, and to life determination for determining the end of life of an atmosphere processing unit of the substrate processing apparatus.

2. Description of the Related Art

In a substrate processing apparatus used to process substrates for fabricating semiconductor wafers, liquid crystal panels and the like, the concentration of various chemical substances in the atmosphere of the apparatus (alkaline, acidic, organic and other components) must be kept as low as possible. In practice, the concentrations of the chemical substances in the apparatus atmosphere (hereinafter frequently called "atmosphere concentrations") are reduced with an atmosphere processing unit using a filter such as chemical filters and activated charcoal filters. A monitor system for monitoring the atmosphere concentrations is also sometimes used.

In some instances it is desirable to monitor the atmosphere concentrations at multiple locations in a single substrate processing apparatus, while in others a need arises to monitor the atmosphere concentrations at multiple locations in two or more substrate processing apparatuses. More often than not, however, the concentration range over which a specific substance must be measured differs among multiple measurement points. This means that different sets of measurement conditions need to be established at the different points. The prior-art atmosphere concentration monitoring systems are of no use in such cases because they cannot effect measurement under different sets of conditions at multiple locations.

In still other cases, measurement using different sets of measurement conditions at a single measurement point may be desirable. This is difficult with the prior-art atmosphere concentration monitoring systems, however, since they cannot easily effect measurement under different sets of conditions at a single measurement point.

The efficiency of the atmosphere processing systems goes down as they process the atmospheric gas, which is air in many cases. The filters of the atmosphere processing systems are to be replaced when their lifetime has passed, accordingly. Since there has been no good technique to determine the end of the life of the atmosphere processing systems, the filters are often replaced with new ones even when their lifetime still remains.

SUMMARY OF THE INVENTION

Accordingly, an object of the present invention is to effect the atmosphere concentration monitoring under different sets of measurement conditions at one or multiple measurement locations.

Another object of the present invention is to determine the life of an atmosphere processing unit of a substrate processing apparatus.

The above and other objects of the present invention are attained at least partly by an atmosphere concentration monitoring system for monitoring a concentration of a specific substance in an atmospheric gas used in a substrate processing apparatus. The system comprises: a plurality of measurement ports for collecting atmospheric gas; a port selection unit for switching among the plurality of measurement ports to select one measurement port at a time; a concentration measurement unit for sampling the atmospheric gas through the measurement port selected by the port selection unit and measuring the concentration of the specific substance contained in the sampled atmospheric gas; and a control unit for controlling the port selection unit and the concentration measurement unit. The control unit comprises: a measurement condition setting unit capable of establishing a different set of measurement conditions for each of the measurement ports; a memory for storing plural sets of measurement conditions established by the measurement condition setting unit, and a control executing unit for controlling the port selection unit and the concentration measurement unit in accordance with the plural sets of measurement conditions stored in the memory.

Since a different set of measurement conditions can be established for each of the plurality of measurement ports, multiple types of measurement can be effected under different sets of measurement conditions while switching among the measurement ports.

According to an aspect of the present invention, the measurement condition setting unit includes a unit for setting a measurement order including a measurement port selection order; and the control executing unit includes a unit for successively executing a series of measurements in accordance with the plural sets of measurement conditions while successively selecting the measurement ports in accordance with the measurement order. This enables measurement to be effected while switching among the measurement ports in the desired order.

The measurement condition setting unit further includes a unit for establishing a set of onetime measurement conditions for conducting a onetime measurement; and the control executing unit effects a measurement in accordance with the set of onetime measurement conditions as interrupt processing in the course of measurements being conducted in accordance with the measurement order when the set of onetime measurement conditions has been established using the measurement condition setting unit. This enables a desired measurement to be effected one time in the course of conducting measurements according to the preset measurement order.

According to another aspect, each set of measurement conditions includes a port number for identifying a measurement port to be used for measurement and a concentration reference value for the specific substance; and wherein the measurement order indicates a selection order of the plural sets of measurement conditions. This enables measurements conducted using the same port to be conducted under different conditions. Processing such as for issuing a warning can be effected when the measured concentration exceeds the concentration reference value.

Preferably, each set of measurement conditions further includes a sampling period for sampling the atmospheric gas. Each set of measurement conditions may further include an analysis period for analyzing a substance collected by the sampling. The measurement accuracy and/or the concentration within which measurement is possible can be adjusted by changing the sampling period and/or the analysis period.

According to still another aspect, the system further comprises a warning issuing unit for issuing a prescribed warning when the concentration of the specific substance measured by the concentration measurement unit exceeds the concentration reference value. This enables prompt response to the problem indicated by the warning.

The specific substance is an alkaline component, for example.

Another atmosphere concentration monitoring system according to the present invention comprises: a measurement port for collecting atmospheric gas; a concentration measurement unit for sampling the atmospheric gas through the measurement port and measuring the concentration of the specific substance contained in the sampled atmospheric gas; and a control unit for controlling the concentration measurement unit. The control unit comprises: a measurement condition setting unit capable of establishing different sets of measurement conditions; a memory for storing the different sets of measurement conditions established by the measurement condition setting unit; and a control executing unit for executing measurements in accordance with the different sets of measurement conditions using the measurement port. Since measurements using the same port can be conducted under different sets of conditions, a series of measurements can be effected in accordance with the different sets of conditions.

The present invention is also directed to a life determination device for determining life of an atmosphere processing unit, which treats an atmospheric gas used in a substrate processing apparatus. The life determination device comprises: a concentration measurement unit for measuring concentration of a specific substance contained in the atmospheric gas at upstream and downstream of the atmosphere processing unit; a flow rate measurement unit for measuring a flow rate of the atmospheric gas passing through the atmosphere processing unit; a throughput calculation unit for integrating with respect to time a product of the flow rate and a difference between the upstream concentration and the downstream concentration, to thereby obtain a throughput of the atmosphere processing unit; and a judgement unit for determining the life of the atmosphere processing unit as a function of the throughput.

The life determination device will accurately determine the throughput of the atmosphere processing unit. A value of the throughput corresponding to the life of the atmosphere processing unit is known in advance. Therefore, the life of the atmosphere processing unit can be determined as a function of the throughput.

According to an aspect of the present invention, the concentration measurement unit comprises: a first measurement port disposed upstream of the atmosphere processing unit; a second measurement port disposed downstream of the atmosphere processing unit; a port selection unit for switching among the first and second measurement ports to select one measurement port at a time; and a concentration analysis unit for sampling the atmospheric gas through the selected measurement port, and measuring the concentration of the specific substance contained in the sampled atmospheric gas. Since a single concentration analysis unit is used to measure the concentration at each measurement port while switching the measurement ports, the size of the device can be reduced.

According to another aspect, the device comprises: a concentration measurement unit for measuring concentration of a specific substance contained in the atmospheric gas at upstream of the atmosphere processing unit; a flow rate measurement unit for measuring a flow rate of the atmospheric gas passing through the atmosphere processing unit; a throughput calculation unit for integrating with respect to time a product of the flow rate and the upstream concentration, to thereby obtain a throughput of the atmosphere processing unit; and a judgement unit for determining the life of the atmosphere processing unit as a function of the throughput. If the downstream concentration is negligible, the throughput of the atmosphere processing unit depends on the upstream concentration but not on the downstream concentration. Therefore the throughput can be determined from the upstream concentration, and the life of the atmosphere processing unit can be accurately determined from the throughput.

The flow rate measurement unit may comprise: an anemometer for measuring a wind speed of the atmospheric gas passing through the atmosphere processing unit; and a flow rate calculation unit for calculating the flow rate by multiplying the wind speed measured by the anemometer and a flow area.

Alternatively, the flow rate measurement unit may comprise: a fan for supplying the atmospheric gas to the atmosphere processing unit; a revolution speed determination unit for determining a revolution speed of the fan; and flow rate calculation unit for calculating the flow rate as a function of the revolution speed.

These and other objects, features, aspects, and advantages of the present invention will become more apparent from the following detailed description of the preferred embodiments with the accompanying drawings.

DESCRIPTION OF THE PREFERRED EMBODIMENT

Figure 1:
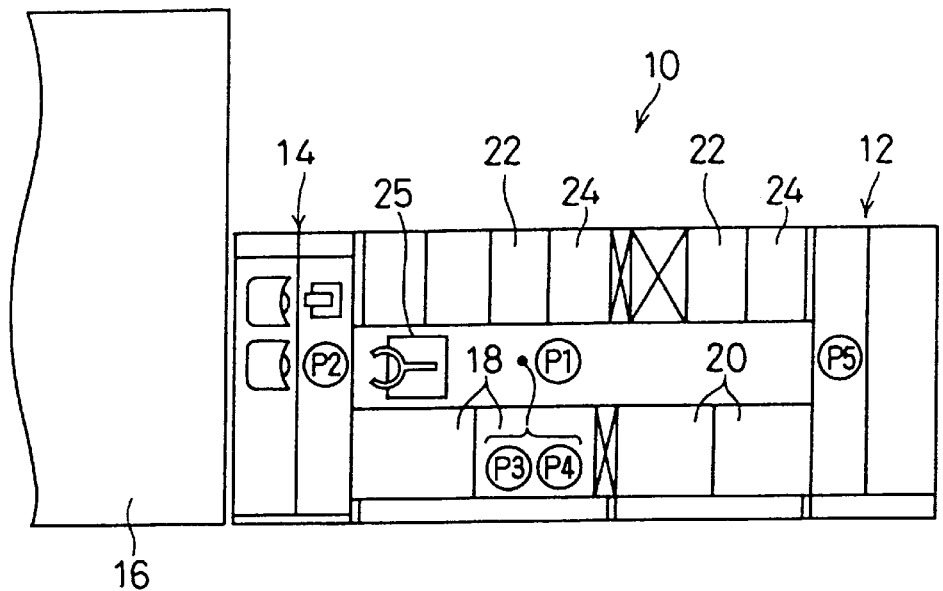
FIG. 1 is a schematic plan view of a substrate processing apparatus incorporating a first embodiment of the invention.
Figure 2:
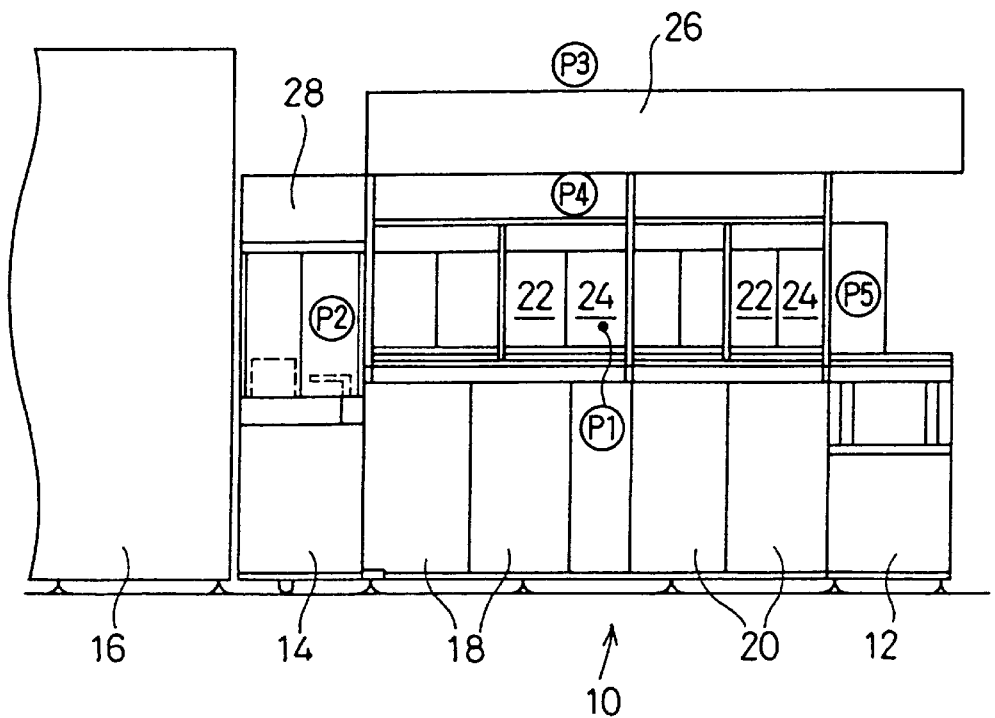
FIG. 2 is a schematic front view of the substrate processing apparatus of FIG. 1.

FIG. 1 is a schematic plan view of a substrate processing apparatus 10 incorporating an embodiment of the invention. FIG. 2 is a schematic front view of the same.

The substrate processing apparatus 10 is equipped with an indexer 12, an interface section 14, a stepper 16, spin coaters 18, spin developers 20, hot plates 22, cool plates 24 and a transporter 25. A cassette containing a number of substrates is set on a stage of the indexer 12. The indexer 12 removes the substrates from the cassette using a transfer device (not shown), stores the processed substrates in the cassette, and effects other such operations. The hot plates 22 and the cool plates 24 are processing units for heating and cooling the substrates to prescribed temperatures. They are provided in vertical stacks each consisting of a plurality of units. The spin coaters 18 coat the substrates with resist or other such liquid agent while spinning them. The spin developers 20 develop the resist by applying developer to the substrate while spinning them. The stepper 16 is a machine for exposing the substrates. The interface section 14 serves to pass substrates between the stepper 16 and the other processing units 18, 20, 22 and 24.

The portion comprising of the indexer 12 and the processing units 18, 20, 22 and 24 will be referred to as the "rotary substrate processing section."

As shown in FIG. 2, the substrate processing apparatus 10 is equipped with a clean ventilator 26 disposed to extend across the space above the rotary substrate processing section. A clean ventilator 28 is similarly installed above the interface section 14. The clean ventilators 26 and 28 blow clean air downward onto the substrate transport path and the processing units in order to maintain their environment clean and consistent.

Figure 3:
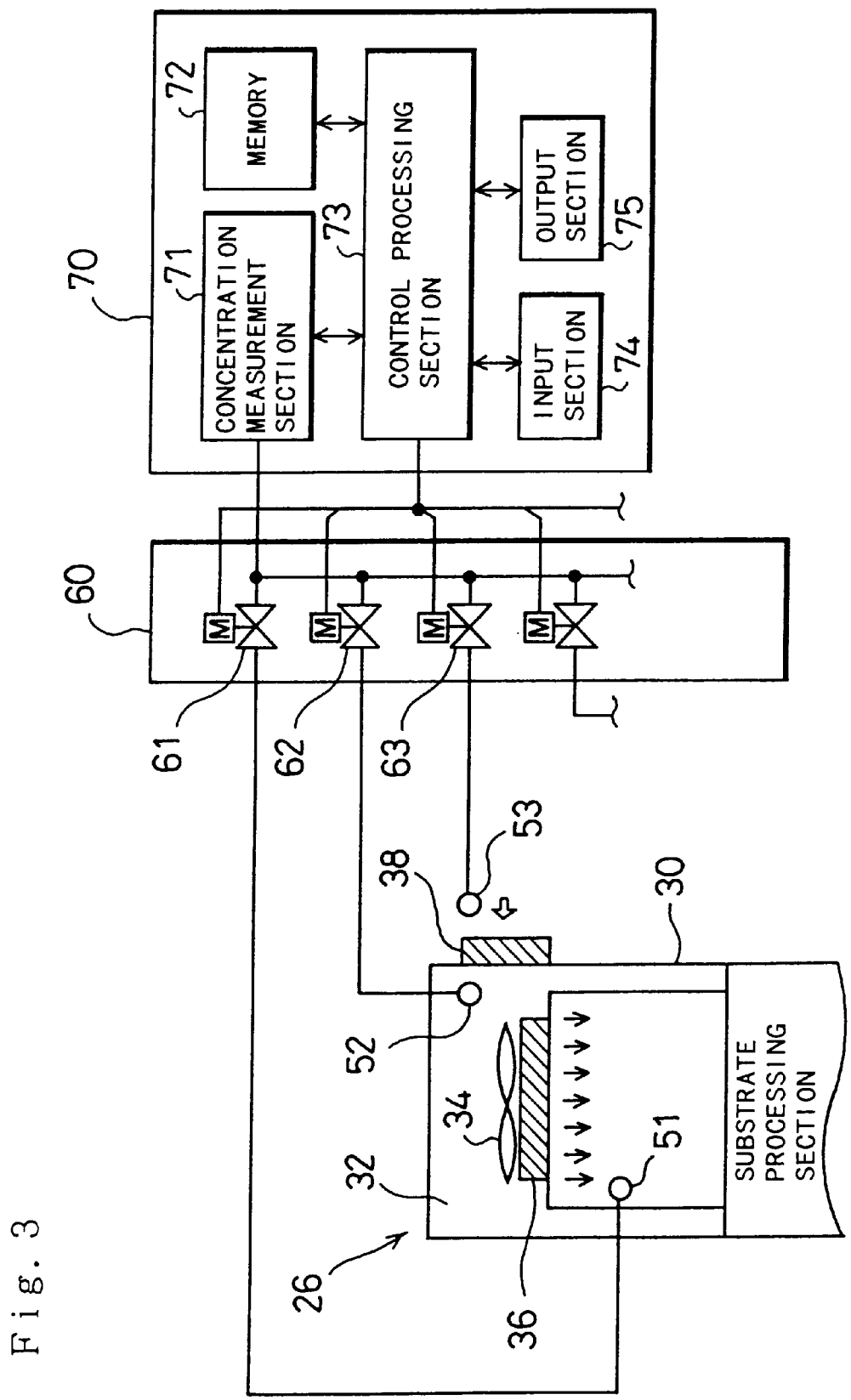
FIG. 3 is a schematic view showing the configuration of an atmosphere concentration monitoring system including multiple measurement ports.

FIG. 3 is a schematic view showing the configuration of an atmosphere concentration monitoring system including multiple measurement ports. The figure shows three measurement ports 51–53 provided near the dean ventilator 26. The measurement ports 51–53 are nozzles for sucking in atmospheric gas. The atmosphere concentration monitoring system comprises multiple measurement ports (including the measurement ports 51–53), a measurement port selector 60, and a measurement controller 70.

As shown in FIG. 3, the clean ventilator 26 has a hollow chamber 32 provided at the top of a column 30. A fan 34 for blowing clean air downward is provided inside the chamber 32 and a secondary filter 36 is installed at an air outlet located downstream of the fan 34. A primary filter 38 is provided at an air intake near the top of the chamber 32 on one side. The fan 34 draws external air into the chamber through the primary filter 38 and blows it through the secondary filter 36 onto the rotary substrate processing section below. The two filters corresponds to an atmosphere processing unit of the present invention.

The first measurement port 51 is situated on the downstream side of the secondary filter 36. The second measurement port 52 is situated between the primary filter 38 and the secondary filter 36. The third measurement port 53 is situated ahead of the primary filter 38 inlet. The "atmospheric gas" is air in many cases.

The chemical substance to be monitored can be selected from among various types including alkaline components such as ammonia, acid components, organic components and the like. When a chemically amplified resist is used in the rotary substrate processing section, it is particularly important to monitor the ammonia concentration and keep it at or below a given tolerable level. A "chemically amplified resist" responds to exposure by producing a specific acid that catalytically amplifies the reaction (decomposition or polymerization) of the exposed portions, thereby enhancing the efficiency of pattern formation. Ammonia or other alkaline components present in the atmospheric gas degrade the quality of the chemically amplified resist by neutralizing the acid it produces. The alkaline component content of the atmospheric gas is therefore preferably held to not more than a specific value. A filter for removing alkaline components (particularly ammonia) is therefore used for at least one of the filters 36 and 38.

The three measurement ports 51–53 shown in FIG. 3 are all used for measuring the concentration of the same chemical substance (e.g., ammonia) but have different concentration measurement ranges. Specifically, the measurement range of first measurement port 51 is lowest, that of the third measurement port 53 is highest, and that of second measurement port 52 is in the middle. In this embodiment, as explained subsequently, a set of measurement conditions can be separately set as appropriate for the concentration measurement range at each measurement port.

Other positions at which measurement ports might be disposed, aside from those indicated in FIG. 3, include the following points indicated in FIGS. 1 and 2: at transport path P1 along which substrates are transported from the stepper 16 to the spin developers 20, at position P2 on the interface section 14, at position P3 outside the substrate processing apparatus 10, at position P4 directly under the filter of the clean ventilator 26, and at position P5 on the indexer 12. As was pointed out above, when a chemically amplified resist is used, the acid generated by the exposure at the stepper 16 should preferably be prevented from reacting with ammonia or other alkaline component. Supervision of alkaline component concentration is therefore particularly important at the first position P1 (transport path along which substrates are transported from the stepper 16 to the spin developers 20) and the second point P2 (on the interface section 14).

The measurement port selector 60 shown in FIG. 3 is equipped with a number of electrically operated valves 61, 62, 62 . . . . The three electrically operated valves 61–63 are connected, one each, with the three measurement ports 51–53. The pipes on the downstream side of the electrically operated valves (on the side of the measurement controller 70) are joined into a single pipe by a manifold. During a measurement, only one of the electrically operated valves is opened and the others are kept closed. Atmospheric gas is sucked through the measurement port connected to the open electrically operated valve into the measurement controller 70.

The measurement controller 70 is a computer system including a concentration measurement section 71, a memory 72, a control processing section 73, an input section 74 and an output section 75. The concentration measurement section 71 measures the concentration of a chemical substance in the atmospheric gas sucked in through the measurement port selector 60. The configuration and operation of the concentration measurement section 71 are explained subsequently. The input section 74 can be a keyboard, touch panel or the like. The output section 75 can be a display means such as a CRT, a printer or the like. The memory 72 is loaded with a computer program for directing the control processing section 73 to conduct various control processing operations. As explained subsequently, the memory 72 also stores various data related to measurement conditions, measurement order and the like.

The measurement port selector 60 corresponds to the port selection means of the atmosphere concentration monitoring system according to the present invention, the concentration measurement section 71 to the concentration measurement means, the input section 74 to the measurement condition setting means, the memory 72 to the memory means, and the control processing section 73 to the control executing means. Strictly speaking, however, some means of the invention are achieved by combining the function of the associated section in FIG. 3 and a function implemented by execution of the computer program loaded in the memory 72 by the control processing section 73.

The computer program which implements the functions of these means is loaded in the main or external memory of the computer system from a floppy disk, CD-ROM or other such portable storage media. Otherwise, it can be loaded into the computer system from a program supply source via a communication line.

In this specification, the term "storage media" is defined to include not only portable media but also RAM, ROM and computer internal memory devices as well as hard disks and other external memory devices connected with the computer. The "storage medium" of this invention can thus be any of various media recorded with a computer program and readable by a computer.

Figure 4:
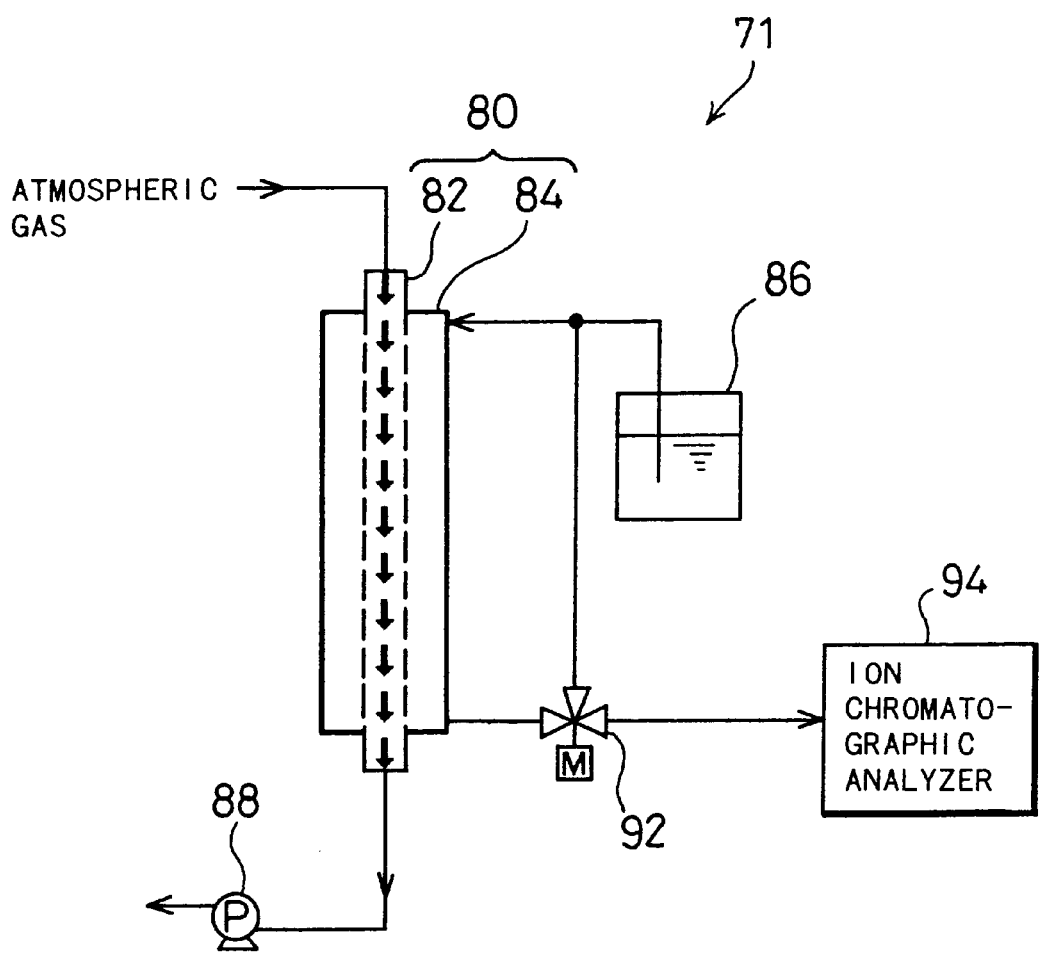
FIG. 4 is a piping diagram showing the internal configuration of a concentration measurement section 71.

FIG. 4 is a piping diagram showing the internal configuration of the concentration measurement section 71. The concentration measurement section 71 has a diffusion scrubber 80, a pure water supply unit 86, an air pump 88, an electrically operated directional control valve 92 and an ion chromatographic analyzer 94. The diffusion scrubber 80 has a double-pipe structure consisting of a porous tube 82 extending along the center axis of a glass pipe 84. When a concentration measurement is not being conducted, pure water supplied from the pure water supply unit 86 is circulated through space between the porous tube 82 and the glass pipe 84. During concentration measurements, this space is filled with pure water supplied from the pure water supply unit 86. Since the pure water supply unit 86 contains an ion exchange resin for removing alkaline, acid and other components that dissolve into the pure water during circulation, it can keep the pure water supplied for circulation constantly clean. After the space between the porous tube 82 and the glass pipe 84 has been filled with pure water, the air pump 88 is operated to suck atmospheric gas in through the measurement port and pass it through the porous tube 82. As the gas flows through the porous tube 82, the specific alkaline component, acid component or other chemical substance to be measured therein passes through the countless pores of the porous tube 82, thereby diffusing from the atmospheric gas into the pure water to be dissolved therein. The directional control valve 92 is then opened to pass the water containing the dissolved chemical substance to the ion chromatographic analyzer 94 to effect concentration measurement. The concentration measurement section 71, used can be used, for example, the IC7000 system manufactured by Yokokawa Analytical Systems.

Figure 5:
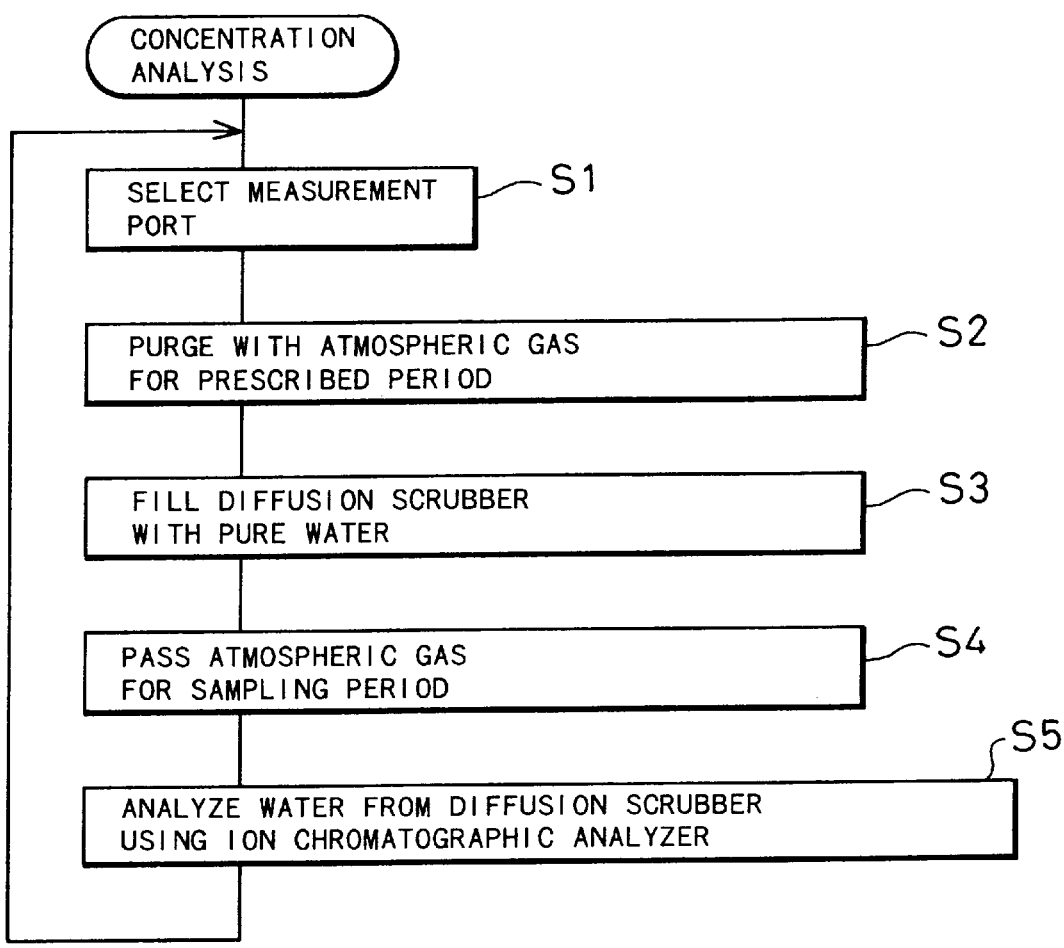
FIG. 5 is a flowchart showing the flow of procedures for effecting concentration analysis by use of multiple measurement ports.

FIG. 5 is a flowchart showing the flow of procedures for effecting concentration analysis by use of multiple measurement ports. In step S1, the control processing section 73 controls the electrically operated valves of the measurement port selector 60 to select one measurement port for use in the measurement. This selection consists in enabling only one measurement port to communicate with the concentration measurement section 71. In step S2, the measurement pipe passage (from the measurement port to the porous tube 82) is purged with atmospheric gas for a prescribed time period. Step S2 is conducted to adjust the interior of the pipes through which the atmospheric gas passes to an initial state appropriate for measurement using the measurement port selected in step S1. On completion of the purging, step S3 is effected to fill the diffusion scrubber 80 with pure water supplied from the pure water supply unit 86. This state is maintained during the following step S4, in which the air pump 88 is operated to pass atmospheric gas through the diffusion scrubber 80 for a sampling period set beforehand. Next, in step S5, the water solution in the diffusion scrubber 80 is sent to and analyzed by the ion chromatographic analyzer 94 to determined the concentration of the specific chemical substance.

Figure 6:
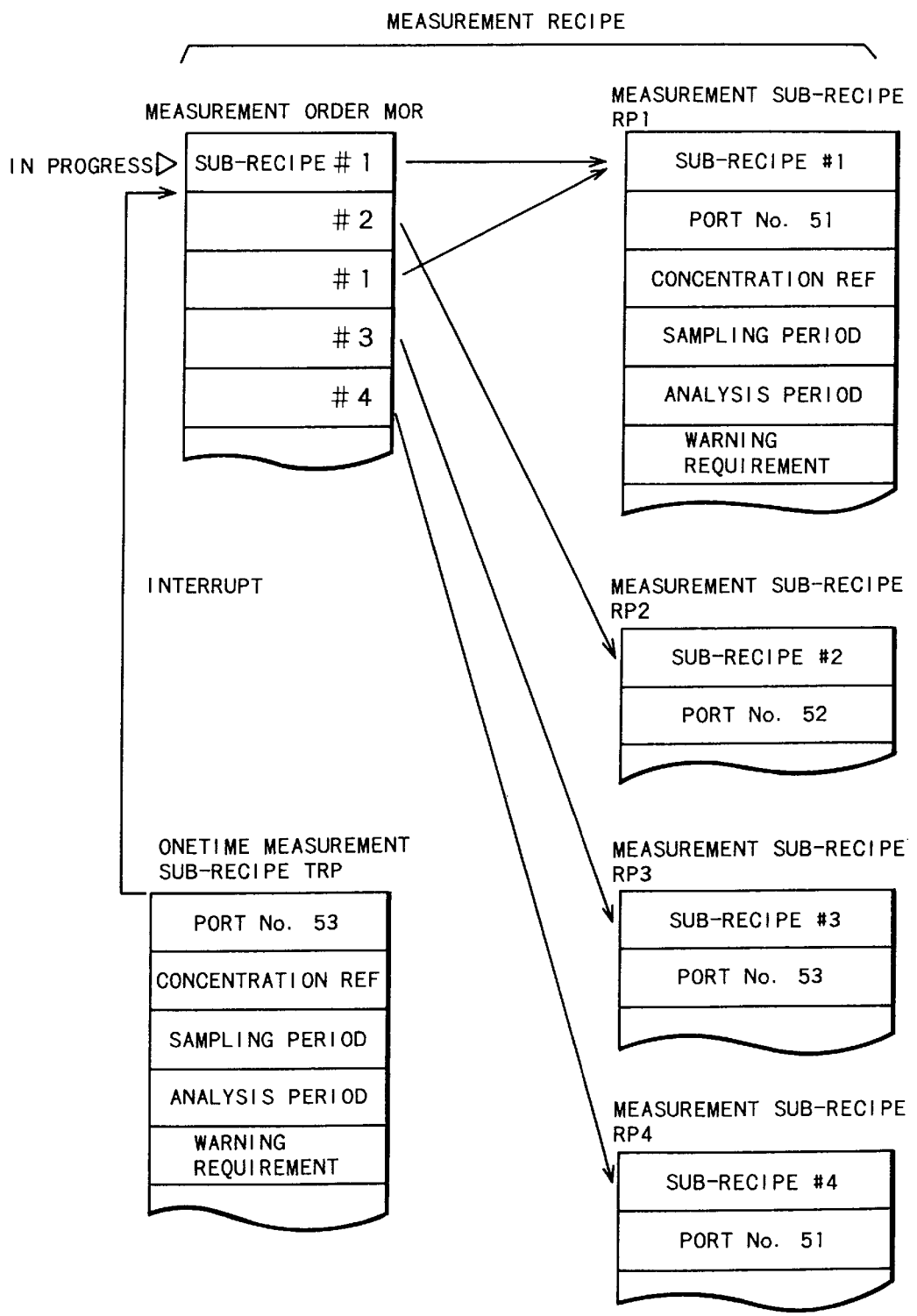
FIG. 6 is an explanatory diagram showing an example measurement recipe.

Measurement recipes defining various sets of conditions for concentration measurement using the multiple measurement ports are stored in the memory 72 of the measurement controller 70 (FIG. 3). FIG. 6 is an explanatory diagram showing an example of a measurement recipe. The measurement recipe includes measurement order MOR and a number of measurement sub-recipes RP1–RP4. Each measurement sub-recipe indicates a set of measurement conditions for a single concentration measurement using one measurement port. Each measurement sub-recipe includes a sub-recipe number, a measurement port number, a concentration reference value, a sampling period, an analysis period and a warning requirement (needed/unneeded) indication. The measurement port number is for identifying one among the multiple measurement ports. The concentration reference value is the basis for deciding whether to issue a prescribed warning. The sampling period is the time period during which atmospheric gas is passed through the diffusion scrubber 80 in step S4 of FIG. 5. The analysis period is the period of time during which analysis is conducted in the ion chromatographic analyzer 94 in step 5. Measurement accuracy generally increases with increasing length of the sampling period and the analysis period.

The measurement order MOR is a list of measurement sub-recipes indicating the order in which the measurement sub-recipes are to be executed. In the concentration analysis processing shown in FIG. 5, the measurement sub-recipes are executed under the conditions defined by each in accordance with the measurement order shown in FIG. 6.

When only one set of measurement conditions is established for each measurement port, the measurement order MOR can be expressed as a list of measurement port numbers rather than a list of sub-recipe numbers. In other words, the measurement order MOR can be of any form so long as it substantially indicates the selection order of the measurement port numbers.

In this specification, the measurement recipe including the measurement order MOR and the multiple measurement sub-recipes RP1–RP4 is called the "broadly defined set of measurement conditions." A single measurement sub-recipe is called a "narrowly defined set of measurement conditions." Other conditions such as the purge period in step S2 (FIG. 5) can also be specified in the narrowly defined sets of measurement conditions. On the other hand, various other conditions can be specified in the broadly defined set of measurement conditions, such as the number of times the measurement sub-recipe measurements are to be repeated daily, the time of day at which the measurement sub-recipe measurements are to be conducted, the time interval between measurements.

The measurement order MOR and the plurality of measurement sub-recipes RP1–RP4 are designated by the operator using the input section 74. Since, as shown in FIG. 6, this embodiment enables different sets of measurement conditions to be established for the individual measurement ports, the measurement using each measurement port can be effected within the most appropriate concentration measurement range for the measurement port concerned. Consider the concentration measurement using the first measurement port 51 in FIG. 3, for example. Since this measurement port is located downstream of the filters 36 and 38 where the ammonia concentration must be reduced as low as possible, the accuracy of the concentration measurement must be raised to the maximum possible. When concentration measurement is conducted using the first measurement port 51, therefore, the sampling period and/or the analysis period is set long to measure relatively low concentration values with high accuracy. Conversely, the third measurement port 53 is located upstream of the filters 36 and 38 in a region which has a relatively high ambient ammonia concentration not requiring particularly strict supervision. The measurement using the third measurement port 53 therefore need only roughly ascertain a relatively high concentration value and can therefore be effected with the sampling period and/or the analysis period is set short.

When a measurement sub-recipe prescribes that warning issuance is needed, a warning is issued when the measured concentration exceeds the concentration reference value. When the concentrations measured at the first measurement port 51 exceeds the concentration reference value, for example, a warning to this effect is issued to inform the operator that the filters need to be replaced. The warning can be issued by, for example, sounding a buzzer or displaying a message on a display means. A configuration enabling issuance of warnings of different types and/or levels can be adopted. These might include one warning requiring the operator to perform a particular task (such as changing the filters) and another that merely calls the operator's attention to a particular situation (such as that the time for changing filters is near).

This embodiment also enables the operator to temporarily suspend the series of concentration measurements being effected in accordance with the measurement order MOR of FIG. 6 so as to conduct a desired concentration measurement as an interrupt operation. For this, the operator uses the input section 74 to enter an instruction for effecting an unscheduled, onetime measurement and specify the measurement conditions of a onetime measurement recipe TRP (FIG. 6). The onetime measurement recipe TRP is the same as a measurement sub-recipe except for the lack of a sub-recipe number. After creating the onetime measurement recipe TRP, the operator enters an instruction to start the onetime measurement. In response to this instruction, the control processing section 73 effects the onetime measurement following completion of the concentration measurement currently in progress. In the example of FIG. 6, the first measurement of the measurement order MOR is in progress so that the onetime measurement is conducted after this first measurement has been completed. Thus this embodiment enables a onetime measurement using a desired measurement port under desired measurement conditions to be effected as interrupt processing in the course of the periodic measurements being conducted in accordance with the preset measurement order MOR. The operator can therefore effect desired concentration measurements whenever found necessary. Such onetime measurements thus provide an easy way to effect, for instance, a particular measurement desired to be conducted only once a month or a measurement desired to be conducted for test purposes. As the one-time measurement recipe TRP it is also of course possible to use one of the measurement sub-recipes stored in the memory 72.

Figure 7:
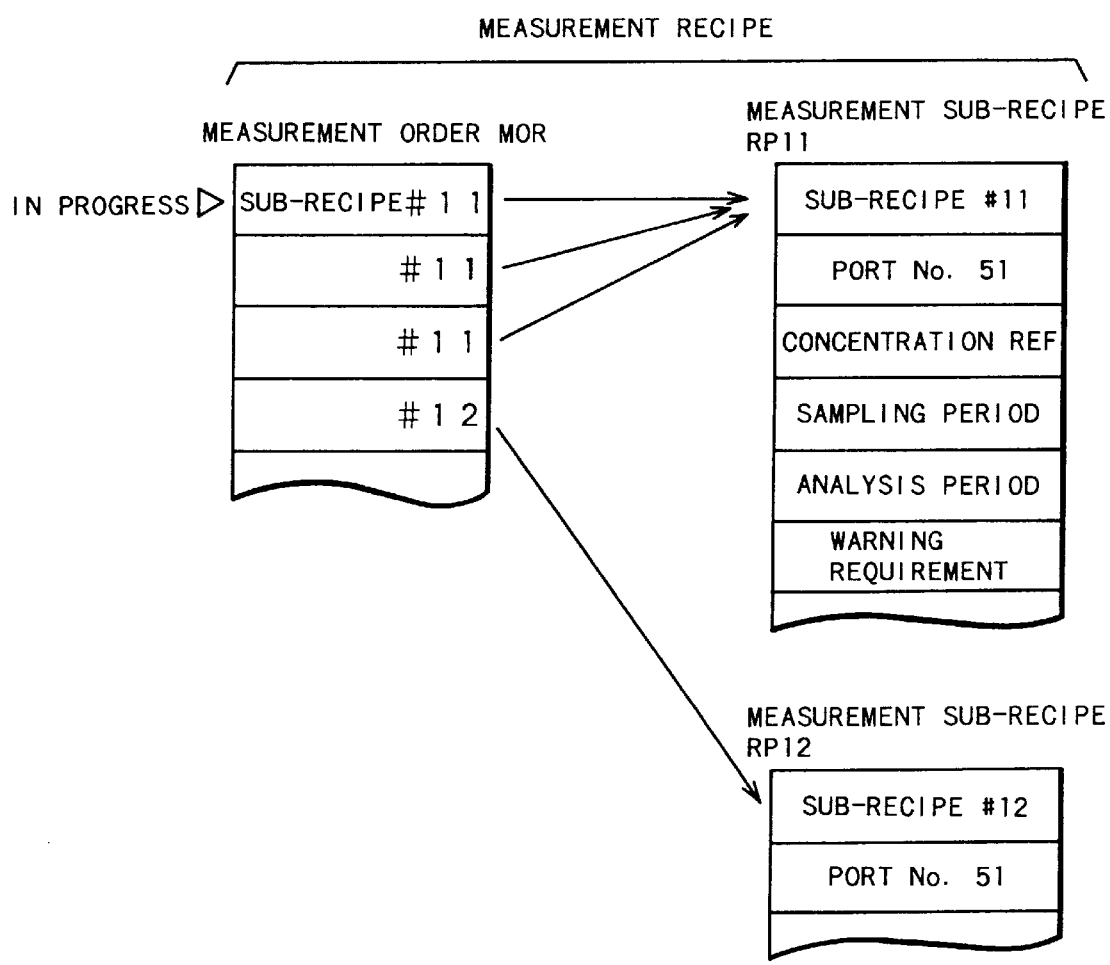
FIG. 7 is an explanatory diagram showing an example of the measurement recipe when measurement is conducted under different sets of measurement conditions using only a single measurement port.

The first embodiment described in the foregoing is advantageous in the point that it enables a combination of multiple measurement sub-recipes to be executed in order to successively effect a series of measurements in a prescribed order, thereby enabling concentration measurements to be conducted continuously with successively selected measurement ports by use of a single concentration measurement section 71. In the manner of the first measurement sub-recipe RP1 and the fourth measurement sub-recipe RP4 shown in FIG. 6, moreover, different sets of measurement conditions can be established for the same measurement port (the first measurement port 51, in the illustrated example). Measurement can therefore be conducted with a high degree of flexibility The atmosphere concentration monitoring system of this embodiment can also conduct measurement under different sets of measurement conditions using only a single measurement port. FIG. 7 is an explanatory diagram showing an example of the measurement recipe in this case. In this example, plural measurement sub-recipes RP11, RP12 are defined for the same measurement port 51. The measurement order MOR designates that the first measurement sub-recipe RP11 is to be executed three times followed by one execution of the second measurement sub-recipe RP12. By this it is possible, for example, to effect the frequently conducted measurement (by the first measurement sub-recipe RP11) roughly using a short sampling and/or analysis period and to effect the infrequently effected conducted measurement (by the second measurement sub-recipe RP12) with high accuracy using a long sampling and/or analysis period. Since this enables measurement using the first measurement port 51 to be effected under different sets of measurement conditions, desired measurement can be conducted in line with the measurement frequency and required accuracy. When only one measurement port is used, the measurement port selector 60 shown in FIG. 3 can be omitted. In this case, the measurement sub-recipe need not include the measurement port number.

Although the first embodiment relates to an example in which multiple ports are provided in a single substrate processing apparatus, the present invention is also applicable in the case where multiple ports are provided in two or more substrate processing apparatuses.

Although the first embodiment relates to an example in which the concentration of one specific substance is measured, the atmosphere concentration monitoring system shown in FIGS. 3 and 4 can also simultaneously measure the concentrations of multiple substances in a single measurement. When the atmospheric concentrations of multiple substances are to be measured, separate concentration reference values are defined for the substances in the measurement sub-recipes.

Figure 8:
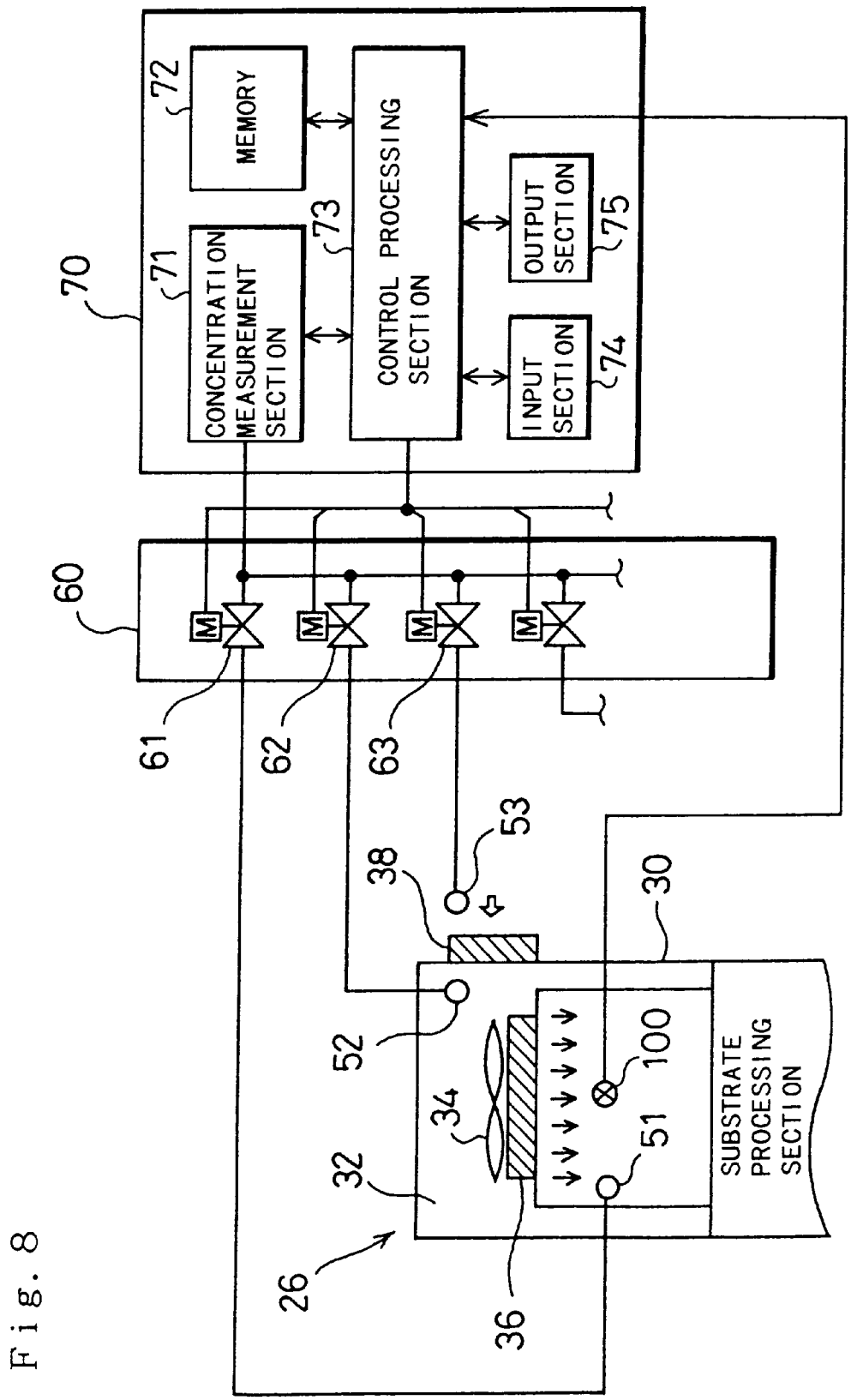
FIG. 8 is a schematic view showing the configuration of an atmosphere concentration monitoring system as a second embodiment of the present invention.

FIG. 8 is a schematic view showing the configuration of an atmosphere concentration monitoring system as a second embodiment of the present invention. This system includes an anemometer 100 downstream of the secondary filter 36 as well as other components shown in FIG. 3. Various types of anemometers can be used such as a differential pressure type and a temperature-measuring type. The wind velocity measured by the anemometer 100 is multiplied by the flow area to measure the flow rate of the atmospheric gas passing through the filters 36, 38. The anemometer 100 may be installed downstream of the primary filter 38.

The anemometer 100 may be installed at plural positions downstream of the secondary filter 36. In this case, the flow rate distribution at the downstream side of the secondary filter 36 can be determined using the wind velocities at the plural positions. Integration of the flow rate distribution over the flow area will give the flow rate more accurately.

The set of measurement ports 51–53 and measurement port selector 60 and concentration measurement section 71 correspond to the concentration measurement means of the life determination device according to the present invention, the measurement port selector 60 corresponds to the port selection means, the concentration measurement section 71 corresponds to the concentration analysis means, and the anemometer 100 corresponds to the flow rate measurement means. Strictly speaking, however, some means of the invention are achieved by combining the function of the associated section in FIG. 6 and a function implemented by execution of the computer program loaded in the memory 72 by the control processing section 73. The functions of the throughput calculation means, the judgement means, and the flow rate calculation means of the present invention are implemented by the control processing section 73.

Figure 9:
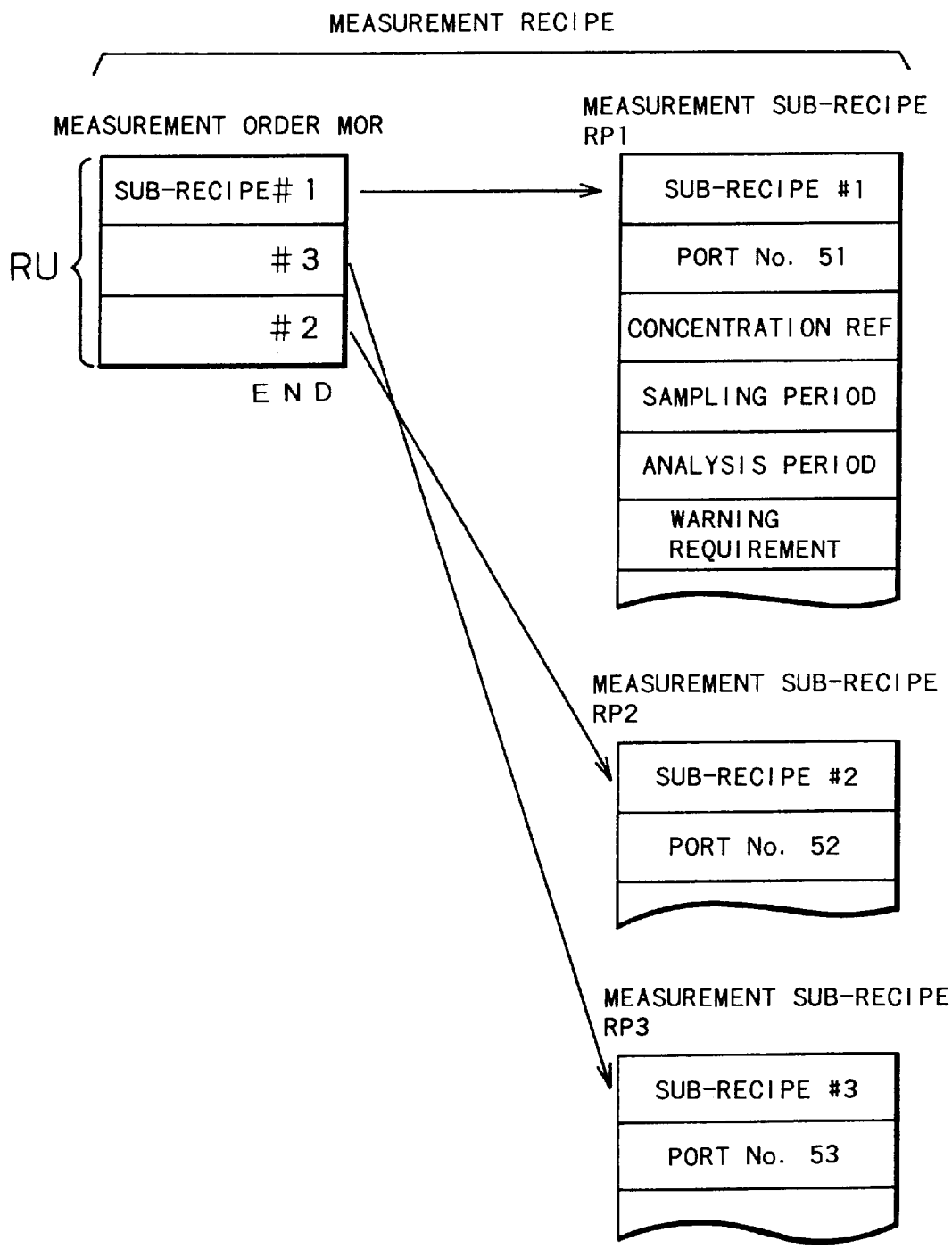
FIG. 9 is an explanatory diagram showing a measurement recipe used in the second embodiment.

FIG. 9 is an explanatory diagram showing an example measurement recipe used in the second embodiment. The measurement recipe includes measurement order MOR and three measurement sub-recipes RP1–RP3. In the measurement order MOR, three pieces of measurement specified by recipe numbers #1, #3, and #2 are set as a single repetition unit RU. After completion of the execution of the repetition unit RU, the same repetition unit RU starts again. The concentrations at the three measurement ports 51–53 are measured as a result of one cycle of the repetition unit RU. The throughput of the filters 38, 36 is calculated using the measured concentrations according to the following Equation (1), for example:

$$W = \sum_t (d_{53} - d_{51}) \cdot V \cdot t \tag{1}$$

where $d_{53}$ denotes a concentration at the third measurement port 53, $d_{51}$ denotes a concentration at the first measurement port 51, V denotes a flow rate, and t denotes a measurement interval. The measurement interval t is a period necessary to execute one cycle of the repetition unit RU. The flow rate V is obtained by multiplying the wind velocity measured by the anemometer 100 and the flow area at the downstream side of the filter 36. Equation (1) means that the throughput W is determined by integrating, with respect to time, a product of the flow rate V and a difference ($d_{53}$–$d_{51}$) of the concentrations at the upstream and downstream sides of the filters 36, 38.

The throughput W fairly accurately indicates a volume of a specific material (ammonia, for example) which has been treated by the two filters 36, 38. The maximum throughput Wmax, which can be treated by the filters 36, 38, is known in advance from the specification of the filters 36, 38. The control processing section 73 compares the throughput W given by the Equation (1) and the maximum throughput Wmax to determine the end of life of the filters 36, 38. ,For example, the output section 75 may issue some warning when the throughput W given by the Equation (1) exceeds a specific value which is obtained by subtracting a prescribed margin from the maximum throughput Wmax (about 80% of Wmax, for example). In this case, the remaining life (about 20% of Wmax) may be also displayed. Alternatively, several different warnings and/or different notifications of remaining life may be issued when the throughput W exceeds several values each related to the maximum throughput Wmax, such as 80%, 90%, and 95% of Wmax. Since the throughput W is close to an actual volume processed by the filters 36, 38, the lifetime of the filters 36, 38 can be determined from the throughput W in high accuracy. The filters 36, 38 can be replaced with new ones at the true end of their life on the basis of the accurate determination of the lifetime of the filters 36, 38, accordingly. As a result, the frequency of the filter change is reduced.

The throughput W1 of the primary filter 38, and the throughput W2 of the secondary filter 36 can be obtained by the following Equations (2) and (3), respectively:

$$W1 = \sum_t (d_{53} - d_{52}) \cdot V \cdot t \tag{2}$$

$$W2 = \sum_t (d_{52} - d_{51}) \cdot V \cdot t \tag{3}$$

These throughputs W1 and W2 will separately determine the life of the respective filters. If the two filters 36, 38 treat different materials, the life of the respective filters can be separately determined by calculating the Equation (1) for the respective materials.

In some cases, the concentration $d_{53}$ downstream of the secondary filter 36 remains almost constant, and its variation is negligible. In this case, the downstream concentration $d_{53}$ in Equation (1) may be replaced with a constant. The throughput W will be determined only from the upstream concentration $d_{51}$, accordingly.

In another case, the concentration $d_{51}$ downstream of the secondary filter 36 is extremely low, and its value is negligible. In this case, the following Equation (4) may be used in place of Equation (1):

$$Wa = \sum_t d_{53} \cdot V \cdot t \tag{4}$$

Equation (4) means that the throughput Wa is determined by integrating, with respect to time, a product of the flow rate V and a concentration $d_{53}$ upstream of the filters 36, 38.

In Equations (1)–(4), the summation of a product of a concentration difference (or a concentration) and the flow rate V and a period t may be replaced with integration of a product of a concentration difference (or a concentration) and the flow rate V with respect to time.

Figure 10:
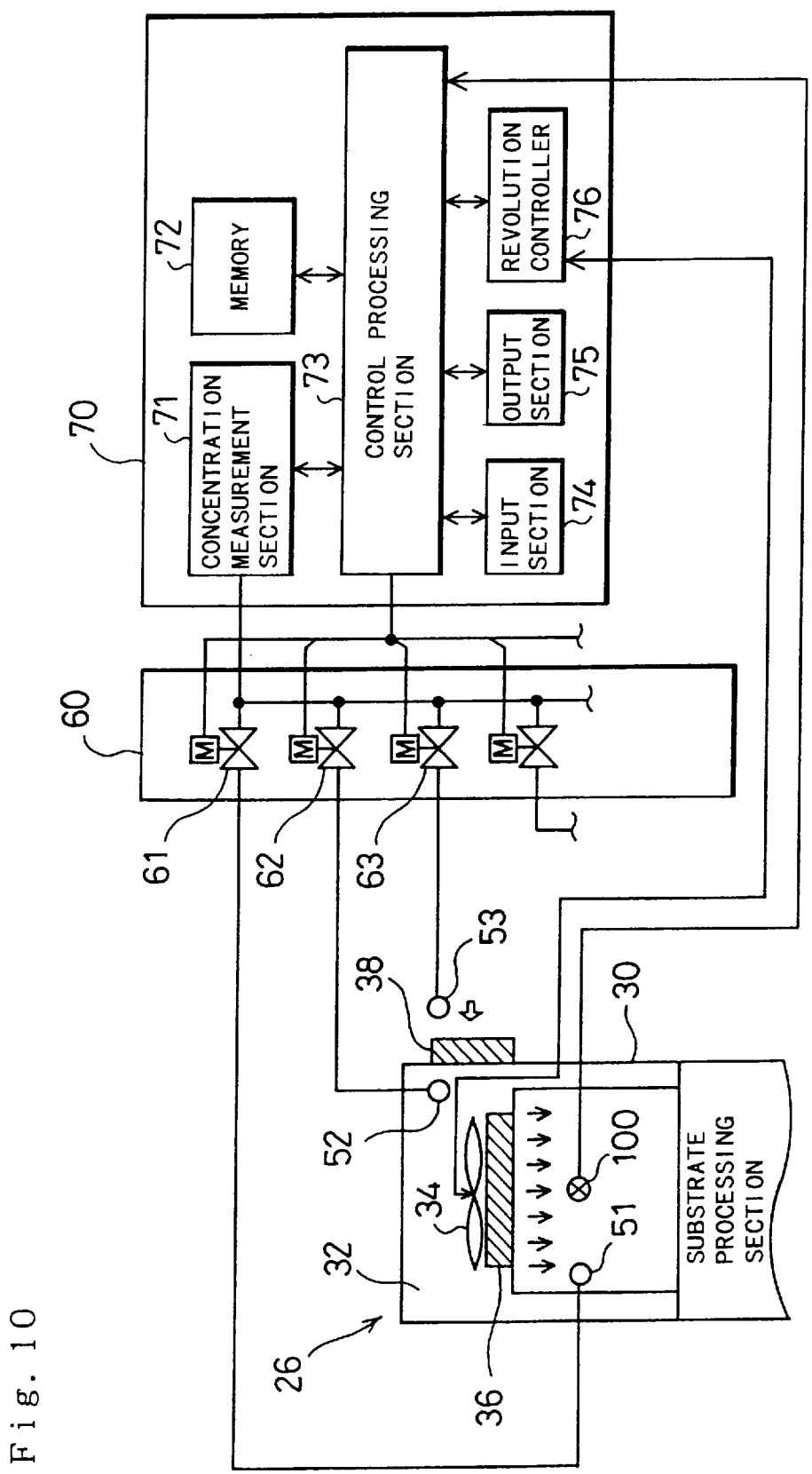
FIG. 10 is a schematic view showing the configuration of an atmosphere concentration monitoring system as a third embodiment of the present invention.

FIG. 10 is a schematic view showing the configuration of an atmosphere concentration monitoring system as a third embodiment of the present invention. This system includes a revolution controller 76 for controlling the revolution speed of the fan 34, as well as other components shown in FIG. 8. The revolution controller 76 rotates the fan 34 at the revolution speed specified by the control processing section 73.

In the structure of FIG. 10, the revolution controller 76 corresponds to the revolution speed determination means of the present invention. Other types of revolution speed determination means may be used such as a rotary encoder.

The revolution speed N of the fan 34 is related to the flow rate V of the atmospheric gas as shown in FIG. 8, for example. The control processing section 73 determines the flow rate V from the revolution speed N on the basis of the relationship, and calculates the throughput according to one of Equations (1)–(4). The anemometer 100 may be omitted if the flow rate is related to the revolution speed N of the fan 34 in advance as described above.

Figure 11:
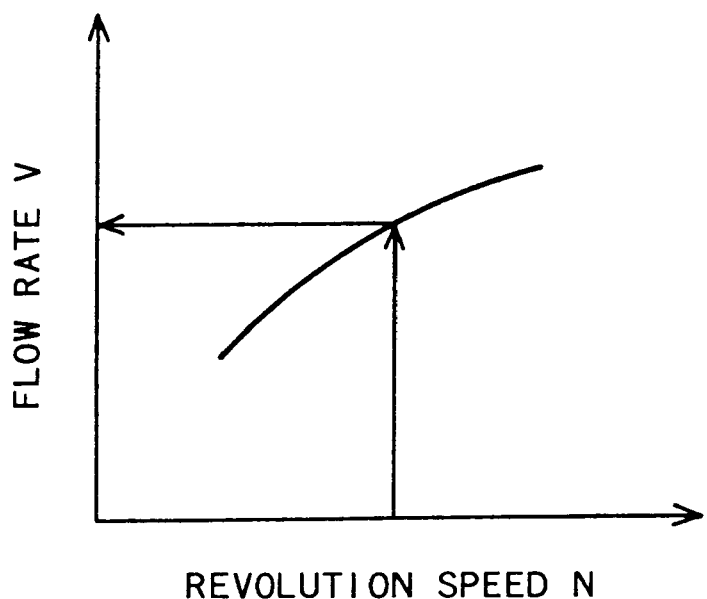
FIG. 11 is a graph showing the relation between the revolution speed of the fan 34 and the flow rate of the atmospheric gas.

Since the relation between the revolution speed N and the flow rate V depends on a pressure drop at the filters 36, 38, it changes as time elapses. In order to solve this problem, the revolution speed N may be adjusted so that the wind speed measured by the anemometer 100, or the flow rate V, is kept at a prescribed value In this case, the flow rate V is calculated from the measured value of the anemometer 100 while not using the relation shown in FIG. 11.

The revolution controller 76 may control the fan 34 to keep its revolution speed N at a prescribed value. In this case, the flow rate V is determined from the revolution speed N, and the throughput is determined according to one of Equations (1)–(4).

In the above embodiment, the actual life of the filters 36, 38 is determined in high accuracy because the throughput of the filters is determined by integrating with respect to time a product of a flow rate and a concentrations difference between upstream and downstream of the filters 36, 38.

In stead of selecting the measurement ports with the measurement port selection sector 60, a plurality of concentration measurement sections 71 may be installed corresponding to a plurality of measurement ports. In this case, the concentration measurement can be simultaneously executed with the plural measurement ports. In the above embodiments, however, the single concentration measurement section 71 sequentially executes the measurement using the plural measurement ports, and the size and the cost of the apparatus can be reduced accordingly.

The present invention is applicable to various types of atmosphere processing units for processing (absorbing or reforming) specific materials, other than the filters described above Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A substrate processing system comprising:
   a substrate processing apparatus including a plurality of processing units for a process using a chemically amplified resist; and
   an atmosphere concentration monitoring apparatus for monitoring a concentration of a specific substance in an atmospheric gas used in the substrate processing apparatus; the atmosphere concentration monitoring apparatus comprising:
   a plurality of measurement ports collecting atmospheric gas;
   port selection means for switching among the plurality of measurement ports to select one measurement port at a time;
   concentration measurement means for sampling the atmospheric gas through the measurement port selected by the port selection means and measuring the concentration of the specific substance comprising an alkaline component contained in the sampled atmospheric gas; and
   control means for controlling the port selection means and the concentration measurement means;
   the control means including:
   measurement conditions setting means capable of establishing a different set of measurement conditions for each of the measurement ports;
   a memory storing plural set of measurement conditions established by measurement condition setting means; and
   control executing means for controlling the port selection means and the concentration measurement means in accordance with the plural sets of measurement conditions stored in the memory;
   the measurement conditions for each of the measurement ports including:
   a port number for identifying a measurement port to be used for measurement;
   a concentration reference value for the specific substance; and a measurement order indicating a selection order of the plural sets of measurement conditions.

2. The substrate processing system according to claim 1, wherein
   the measurement condition setting means includes means for setting a measurement order including a measurement port selection order; and
   the control executing means includes means for successively executing a series of measurements in accordance with the plural sets of measurement conditions while successively selecting the measurement ports in accordance with the measurement order.

3. A substrate processing system comprising:
   a substrate processing apparatus including a plurality of processing units for a process using a chemically amplified resist; and
   an atmosphere concentration monitoring apparatus for monitoring a concentration of a specific substance in an atmospheric gas used in the substrate processing apparatus;
   the atmosphere concentration monitoring apparatus comprising:
   a plurality of measurement ports collecting atmospheric gas;
   port selection means for switching among the plurality of measurement ports to select one measurement port at a time;
   concentration measurement means for sampling the atmospheric gas through the measurement port selected by the port selection means and measuring the concentration of the specific substance comprising an alkaline component contained in the sampled atmospheric gas; and
   control means for controlling the port selection means and the concentration measurement means;
   the control means including:
   measurement conditions setting means capable of establishing a different set of measurement conditions for each of the measurement ports;
   a memory storing plural set of measurement conditions established by measurement condition setting means; and
   control executing means for controlling the port selection means and the concentration measurement means in accordance with the plural sets of measurement conditions stored in the memory;
   further, herein the measurement condition setting means further includes means for establishing a set of onetime measurement conditions for conducting a onetime measurement; and wherein
   the control executing means effects a measurement in accordance with the set of onetime measurement conditions as interrupt processing in the course of measurements being conducted in accordance with measurement order when the set of onetime measurement conditions has been established using the measurement condition setting means.

4. The substrate processing system according to claim 1, wherein each set of measurement conditions further includes a sampling period for sampling the atmospheric gas.

5. The substrate processing system according to claim 4, wherein each set of measurement conditions further includes an analysis period for analyzing a substance collected by the sampling.

6. The substrate processing system according to claim 1, further comprising warning issuing means for issuing a prescribed warning when the concentration of the specific substance measured by the concentration measurement means exceeds the concentration reference value.

7. A substrate processing system comprising:

a substrate processing apparatus including a plurality of processing units for a process using a chemically amplified resist; and an atmosphere concentration monitoring apparatus for monitoring a concentration of a specific substance in an atmospheric gas used in the substrate processing apparatus;

the atmosphere concentration monitoring apparatus comprising:

a plurality of measurement ports collecting atmospheric gas;

a port selector selecting one of the plurality of measurement ports;

a concentration measurement unit sampling the atmospheric gas through the selected measurement port and measuring the concentration of the substance comprising an alkaline component contained in the sampled atmospheric gas; and a controller controlling the port selector and the concentration measurement unit;

the controller including:

a measurement condition setting device capable of establishing a different set of measurement conditions for each of the measurement ports;

a memory storing plural sets of measurement conditions established by the measurement condition setting device; and a control executing device controlling the port selector and the concentration measurement unit in accordance with the plural sets of measurement conditions stored in the memory;

the measurement conditions for each of the measurement ports including:

a port number of identifying a measurement port to be used for measurement;

a concentration reference value for the specific substance; and a measurement order indicating a selection order of the plural sets of measurement conditions.

* * * * *